United States Patent [19]

Berthel et al.

[11] Patent Number: 4,514,758
[45] Date of Patent: Apr. 30, 1985

[54] FALL VELOCITY INDICATOR/VIEWER

[75] Inventors: Robert O. Berthel, Windham, N.H.; Vernon G. Plank, Mansfield, Mass.; Stephen H. Jones, Weston, Mass.; Anthony J. Matthews, Salisbury, Mass.

[73] Assignee: The United States of America as represented by the Secretary of the Air Force, Washington, D.C.

[21] Appl. No.: 442,496

[22] Filed: Nov. 18, 1982

[51] Int. Cl.³ .............................................. H04N 7/18
[52] U.S. Cl. ..................................... 358/93; 358/107; 358/108; 356/28
[58] Field of Search ................. 358/93, 100, 106, 107, 358/108, 229, 225; 356/441, 442, 28.5, 28; 250/222.2, 223 R, 239; 73/432 PS; 377/10, 11

[56] References Cited

U.S. PATENT DOCUMENTS

| | | |
|---|---|---|
| 417,357 | 12/1889 | Fergusson . |
| 1,877,713 | 12/1929 | Beck . |
| 2,721,495 | 3/1952 | Schaefer .............................. 88/14 |
| 2,954,690 | 3/1952 | Dickinson ........................... 73/171 |
| 3,275,744 | 10/1962 | Dietrich .................................. 178/6 |
| 3,390,229 | 11/1962 | Williams ................................ 178/6 |
| 3,589,813 | 1/1968 | Sturzinger .......................... 356/72 |
| 3,614,231 | 2/1968 | Shaw ..................................... 356/37 |
| 3,801,779 | 4/1974 | Ver Sluis ............................ 250/222 |
| 3,914,053 | 10/1975 | Morley et al. ...................... 356/37 |
| 4,136,950 | 1/1979 | Labrum et al. ..................... 358/107 |
| 4,162,509 | 7/1979 | Robertson ............................ 356/28 |
| 4,305,658 | 12/1981 | Yoshida ................................ 356/23 |

FOREIGN PATENT DOCUMENTS 2012948 8/1979 United Kingdom ............ 73/432 PS

Primary Examiner—John C. Martin
Assistant Examiner—Edward L. Coles
Attorney, Agent, or Firm—Donald J. Singer; Jacob N. Erlich

[57] ABSTRACT

A fall velocity indicator/viewer having a sampling compartment, a camera system, and an elongated tunnel for interconnecting the camera system to the sampling compartment. The camera system includes a video camera for continuously monitoring snowflakes as they naturally fall through a viewing area in the sampling compartment. The snowflakes are illuminated by a pair of strobe lights directly and in combination with reflected light from a pair of mirrors. In addition, a mirror in the tunnel provides a reflected view from the top of the snowflakes. The video camera is capable of thereby monitoring multiple views of snowflakes in a single video frame and provide sufficient data to analyze the physical characteristics of the snowflakes as well as aid in making velocity determinations and other observations of naturally falling snowflakes.

17 Claims, 3 Drawing Figures

FALL VELOCITY INDICATOR/VIEWER

STATEMENT OF GOVERNMENT INTEREST

The invention described herein may be manufactured and used by or for the Government for governmental purposes without the payment of any royalty thereon.

BACKGROUND OF THE INVENTION

This invention relates generally to devices capable of determining fall velocities of hydrometeors, and, more particularly, to a fall velocity indicator/viewer which is extremely reliable in determining the velocity of naturally falling snowflakes as well as providing a clear observation area for viewing the naturally falling snowflakes.

It has long been recognized that electro-optical and communication systems are especially susceptible to attenuation because of falling snow. In addition to falling snow, other types of hydrometeors or particulate matter can have an adverse affect on electro-optical and microwave systems as well as other communication systems. Therefore, it becomes extremely important to document not only the velocity of such naturally falling hydrometers such as snowflakes, but also to observe, at close range, the snowflake itself. By analyzing information based upon the oscillation of snowflakes, the conditions at which they tumble, the specific type of crystals that transverse a point along a line of sight, and the relationship between fall speed and particle size, steps may then be taken to lessen the attenuation effects caused by naturally falling hydrometeors such as snowflakes. In addition, it is essential that the above observations and determinations be made with "naturally falling" hydrometeors, and not be limited to only snowflakes but also include other hydrometeors such as rain, drizzle, hail, graupel and freezing rain.

Heretofore, devices utilized in determining the velocity of falling objects were lacking in many of the areas recited above. Consequently, it is becoming increasingly essential to develop a device which not only is able to accurately and reliably determine fall rate velocity, but is also capable of providing a clear and accurate observation area in order to study the hydrometeors under naturally occuring conditions.

SUMMARY OF THE INVENTION

The present invention overcomes the problems encountered in the past and as set forth above by providing a fall velocity indicator/viewer which accurately provides a means of obtaining velocity information as well as visual information about "naturally falling" hydrometeors, and, snowflakes, in particular.

The fall velocity indicator/viewer of this invention incorporates therein the use of video recording instruments in order to continually monitor snowflakes as they naturally tumble and fall through a preselected viewing area. This viewing area is situated within an enclosed sampling compartment. A port located on the top of the sampling compartment permits "naturally falling" snowflakes to enter the field of view. The size of the port is adjustable and can be varied in accordance with the desired field of view.

A collar is centered about the port to prevent the entry of accumulated snow from the top of the compartment. In addition, the height of the collar is adjustable in order to limit the sampled snowflakes to particles having fall trajectories within a specified range or angle. For example, it is desirable to limit the sampling of snowflakes to naturally falling snow having trajectories of less than 45° from the vertical.

Lighting of the falling snow is provided by a pair of strobe lights or lamps located below the lower corners of the viewing area in conjunction with reflected strobe light received from a pair of mirrors situated at the upper corners of the sampling compartment adjacent the viewing area. This arrangement provides uniform lighting throughout the sampling or viewing area. The strobe lighting produces multiple frontal images on single video frames enabling fall velocities to be calculated by relating the flash rate of the strobe lamps with the fall distance of the snowflakes.

In addition, another mirror is positioned substantially adjacent to and above the viewing area in optical alignment with a video camera to provide a reflection of the top of the snowflakes as they fall. Therefore, the upper portion of the video frame images a reflection from this mirror which is angled to give a downward looking view of the falling snowflakes. The combination of the front and top views yield information as to orientation characteristics (tumbling, oscillation, etc.), crystal-type, size and fall velocity.

A connecting tunnel optically interconnects the viewing area to the video camera located within a temperature controlled enclosure. Preferably the angled mirror referred to hereinabove is located within the connecting tunnel. A conventional video recorder is utilized to record the images provided by the video camera for appropriate analysis of fall velocity and observation of snowflake activity. Strobe frequency is adjusted to provide the desired number of particle images on a single video frame.

In addition to the observation of hydrometeors, such as snowflakews, the present invention is also capable of monitoring the fallout from any natural or man made conditions, such as volcanic eruptions, explosions, sand storms and smoke stack emissions.

It is therefore an object of this invention to provide a fall velocity indicator/viewer which provides a continuous recording of "naturally falling" snowflakes and/or other hydrometeors.

It is another object of this invention to provide a fall velocity indicator/viewer which is capable of determining the fall velocity or rate of fall of individual particulate matter.

It is a further object of this invention to provide a fall velocity indicator/viewer which is capable of determining variations in sizes and orientation of naturally falling particles.

It is still a further object of this invention to provide a fall velocity indicator/viewer which is capable of providing multiple images of individual particles on a single video frame.

It is an even further object of this invention to provide a fall velocity indicator/viewer which is economical to produce and which utilizes conventional, currently available components that lend themselves to standard mass producing mass manufacturing techniques.

For a better understanding of the present invention, together with other and further objects thereof, reference is made to the following description taken in conjunction with the accompanying drawing and its scope will be pointed out in the apended claims.

DETAILED DESCRIPTION OF THE DRAWING

DETAILED DESCRIPTION OF THE PREFERRED EMBODIMENT

Figure 1:
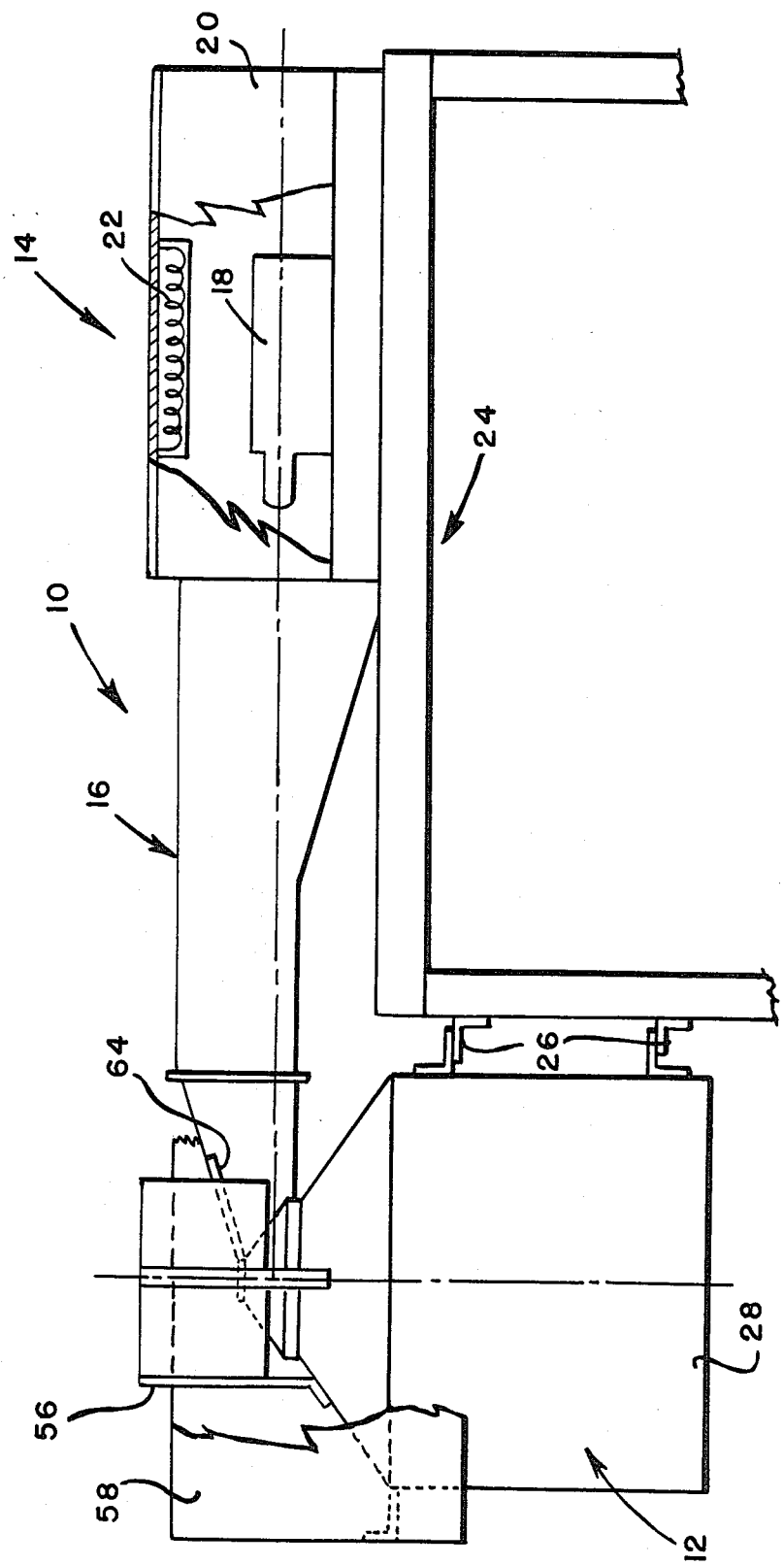
FIG. 1 is a side elevational view, shown partly in segmented fashion, of the fall velocity indicator/viewer of this invention.

Reference is now made to FIG. 1 of the drawing which clearly depicts an overall view of the fall velocity indicator/viewer 10 of the present invention. Fall velocity indicator/viewer 10 of this invention is made up of three major components; (1) a sampling compartment 12, (2) a camera system 14, and (3) an elongated tunnel 16 for interconnecting camera system 14 to the sampling compartment 12.

More specifically, camera system 14 includes a conventional video camera 18 such as RCA Model TC 1005/01 Vidicon located within a temperature controlled enclosure 20. The lens (preferably a zoom-type magnification lens) on video camera 18 is aimed horizontally through an opening (not shown) within an end of the enclosure 20, through tunnel 16 and into the sampling compartment 12 by way of an aperture 21 located within the upper portion of sampling compartment 12. The video camera 18, which is located within enclosure 20, is electrically heated by any conventional variable heater element 22 situated therein. Heater 22 maintains a proper operating temperature condition for camera 18 even though the entire fall velocity indicater/viewer 10 is situated outdoors and in less than desirable operating temperature conditions. The enclosure 20 is mounted upon a rigid support table 24 to which is connected by any suitable securing elements such as brackets 26 sampling compartment 12.

Figure 2:
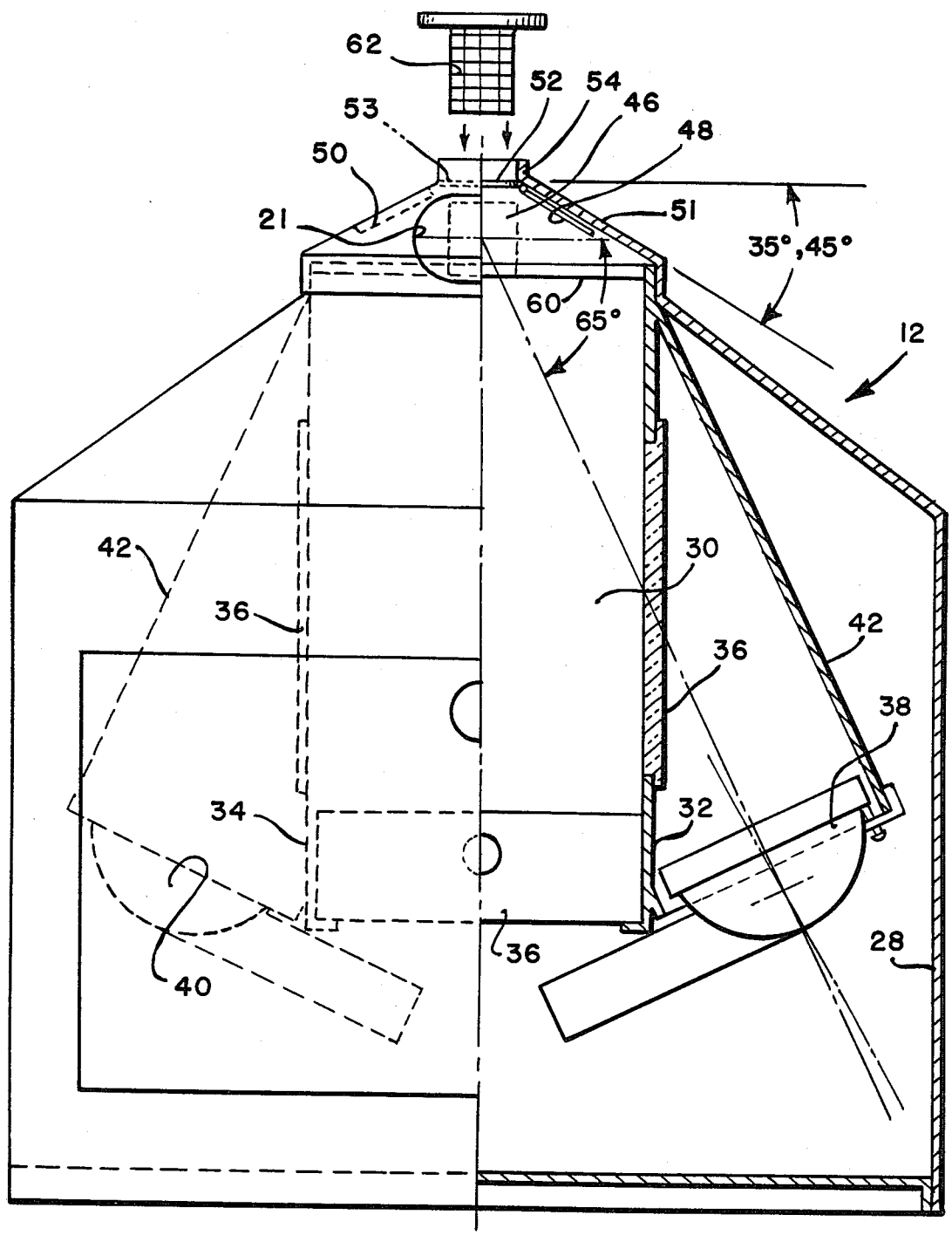
FIG. 2 is a side elevational view of the sampling compartment of the fall velocity indicator/viewer of this invention and shown partly in cross-section.

Referring now to FIGS. 1 and 2 of the drawing, sampling compartment 12 is shown as having an outer housing 28 which encloses an inner housing 30 also referred to as the sampling chamber. Inner housing or sampling chamber 30 has a pair of walls 32 and 34, which each include, as a portion thereof, a section made of a transparent material 36 such as plexiglass. In addition, the bottom of inner housing 30 has a tray 36 slidably removable therein. Tray 36 is utilized to collect the viewed snowflakes and can be removed through a door 37 within outer housing 28.

A pair of conventional high intensity strobe lamps 38 and 40 (such as General Radio Model GR 1538-A strobe lamps) are mounted by any suitable support frames 42 to inner housing 30. The strobe lamps 38 and 40 are located adjacent the bottom corners of outer housing 28 and angled so as to shine through the transparent material 36 of walls 32 and 34, respectively, and onto a sample viewing area 46 which will be described in greater detail hereinbelow. An acceptable angle with respect to the horizontal for the positioning of strobe lamps 38 and 40 would be 65° degrees, although this angle may vary within the scope of the invention.

To sufficiently illuminate viewing area 46 a pair of mirrors 48 and 50 are positioned within a pyramid-shaped upper portion 51 of sampling compartment 12 adjacent viewing area 46. Mirrors 48 and 50 are preferably positioned 35° to 45° from the horizontal. The light emitted by strobe lamps 38 and 40 when combined with the reflected light from mirrors 48 and 56 provide a high degree of illumination of viewing area 46.

Entrance to sampling compartment 12 by falling snowflakes takes place through a port 52 located at the top of compartment 12. Port 52 may be made adjustable in diameter by means of a movable shutter-like, aperture plate 53 in order to control the amount of snowflakes passing through the viewing area 46. Since the concept behind the fall velocity indicator/viewer 10 of the present invention is to monitor "naturally falling" snowflakes contrasted to wind driven or blowing snow, an adjustable wind baffle 54 is positioned about port 52. Consequently, only those snowflakes having fall trajectories of less than 45 degrees from the vertical are capable of entering port 52. Further, as clearly illustrated in FIG. 1 of the drawing, a series of baffles 56 and 58 are provided around port 52 in order to decrease occasional wind-pumping effects which may adversely affect the receipt of falling snowflakes.

Reference is now made specifically to the viewing area 46 which is located within the pyramid-shaped upper portion 51 of the sampling compartment 12. The viewing area is located adjacent aperture 21 and is centrally located within the upper portion 51 of sampling compartment 12. Its preferred dimension is 3 cm$^2$. Although not limited to the particular dimensions stated above and below, viewing area 46 is located approximately 75 cm from the lens of the video camera 18. With the type of equipment utilized with the present invention, this distance restricts the optical depth of field to approximately 1.5 cm. In addition two wires 60 (only one of which is shown in FIG. 2) may be connected to the compartment housing and positioned at the lower boundary of viewing area 46 in order to deliniate the limits of the optical field of depth.

Mirrors 48 and 50 are positioned above the sampling or viewing area 46 so as to provide reflections from strobe lamps 38 and 40, therefore clearly illuminating viewing area 46. In addition, reference lines to aid in the determination of the fall speed of snowflakes in a manner indicated below are provided by means of a removable transparent grid 62. Grid 62 can be placed within port 52 when initial readings are taken in order to calibrate the optical system for the subsequent determination of distance between adjacent snowflake images. This distance is utilized at a later time in making velocity determinations.

As shown in FIG. 1, camera system 14 is optically aligned with viewing area 46 through connecting tunnel 16. Connecting tunnel 16 is preferably made of sheet metal and is utilized to prevent ambient light, snow and wind, etc. from degrading the quality of the viewing and therefore permitting accurate data from being obtained by this invention. The interior surfaces of tunnel 16 as well as those surrounding viewing area 46 are painted of an absorbant color such as flat black. In addition, a mirror 64 (see FIG. 1 of the drawing) is mounted in the upper portion of tunnel 16 adjacent aperture 21 and viewing area 46. Mirror 64 is angled such that camera 18 can view the top as well as the front of the snowflakes transitting the sample viewing volume or area 46.

Figure 3:
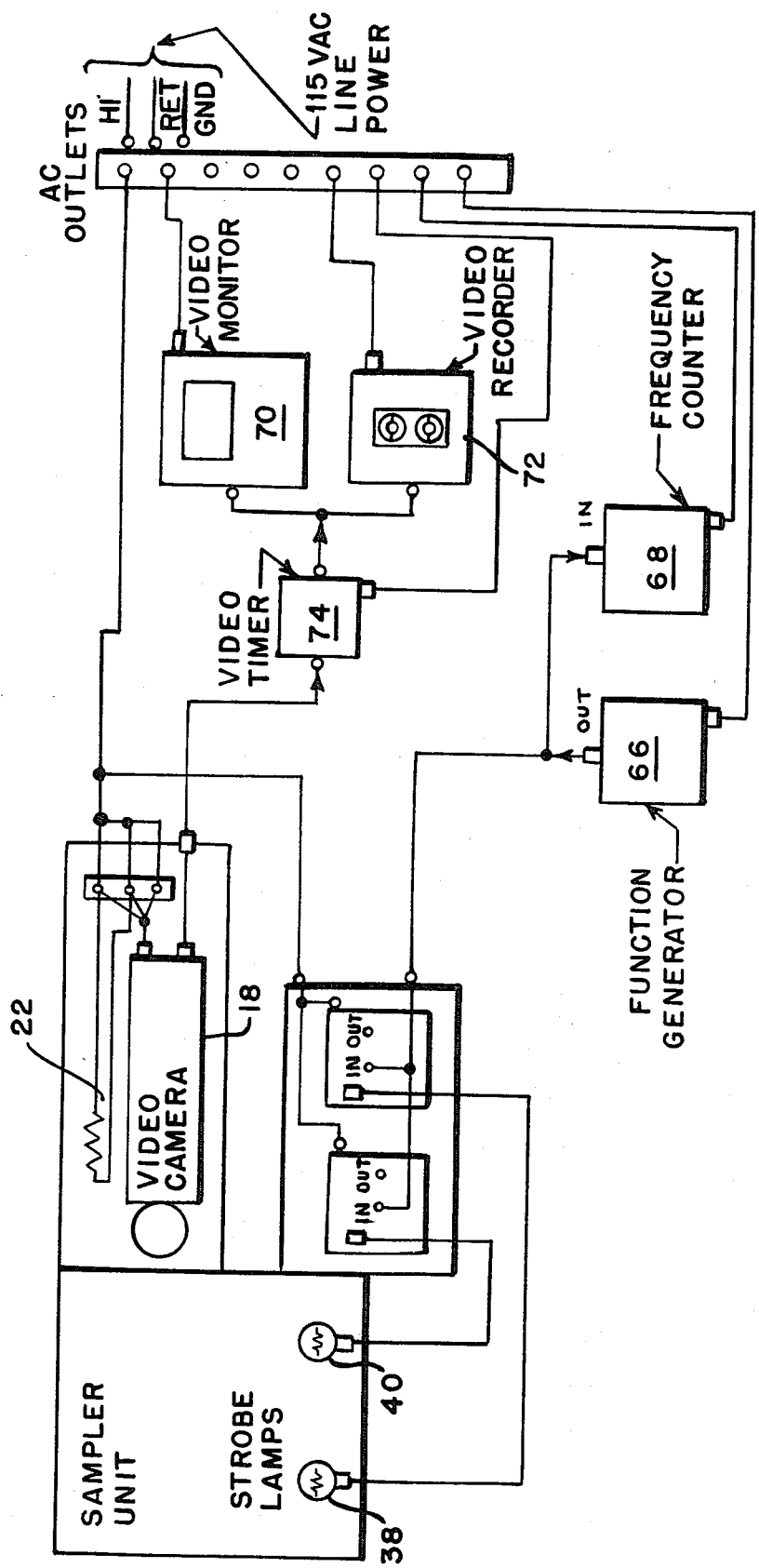
FIG. 3 is a schematic representation of the electrical circuitry utilized with the fall velocity indicator/viewer of this invention.

Reference is now made to FIG. 3 of the drawing which schematically illustrates the various electrical components which make up the fall velocity indicator/viewer 10 of the present invention. Electrical components include a conventional adjustable function generator 66, frequency counter 68, TV monitor 70, video cassette recorder 72 and a counter/timer 74. The adjustable function generator 66 is used to externally trigger the strobe lamps 38 and 40. The frequency counter 68 visually displays the precise strobe rate. The counter/timer 74 provides the video frame count to both TV monitor 70 and the cassette recorder 72.

MODE OF OPERATION

During operation of the fall velocity indicator/viewer 10 of this invention snowflakes falling through port 52 and into sample viewing area 46 are detected by the video camera 18 only when illuminated by the strobe lamp flashes. Since the selected strobe rate is designed to exceed the camera's video scan rate, the TV monitor 70 and cassette recorder 72 are able to display and record multiple images of a snowflake or other particulate matter on a single frame as it transits the sample viewing area 46. Thus, a recorded video frame may show the top view of a snowflake (reflected by the top angled mirror 64) followed by two or more frontal images. Comparing top and frontal images can provide information of particle orientation, tumbling or oscillation.

Calculation of the fall speed is determined by means of initially inserting the removable grid 62 in place within the viewing area 46. The recorded image serves to calibrate the overall optical system for the magnification of the optical system. When a snowflake or particle falls through the viewing area 46 several images are formed on a single video frame. The distance the particle falls is measured from a photo of the TV recording and adjusted for magnification through the use of the photo of the calibrated grid 62. The time is determined through the knowledge of the flash rate of strobe lamps 38 and 40. Measuring the distance an individual particle travels between images and knowing the strobe rate or time between images, the fall velocity can be easily computed. In addition, the recorded video data also provides particle size and type information.

Although the fall velocity indicator/viewer 10 of the present invention is primarily used for the analysis of snowflakes, it may be used for any type of hydrometeors or particulate matter when it is essential to observe particle motion under natural conditions. Strobe speed and optical magnification can be varied within the scope of this invention to compensate for different fall speeds and particle sizes. Other hydrometeors such as rain, drizzle, hail, graupel and freezing rain can also be easily monitored by the present invention. Other uses for the present invention include the monitoring of fallout from any natural or man made conditions such as volcanic eruptions, explosions, sandstorms and smoke stack emission.

Although this invention has been described with reference to a particular embodiment, it will be understood that this invention is also capable of further and other embodiments within the spirit and scope of the apended claims.

We claim:

1. A fall velocity indicator/viewer comprising:
a sampling compartment, said sampling compartment having an adjustably-sized port in the top portion thereof for allowing free falling particulate matter to pass therethrough and through a viewing area of preselected dimensions;
means located within said sampling compartment for providing a source of light at predetermined intervals of time, said light providing means being positioned so as to illuminate said free falling particulate matter as it is falling through said viewing area;
means located within said sampling compartment for reflecting said light in order to aid in the illumination of said free falling particulate matter in said viewing area during said predeteremined intervals of time;
means positioned a preselected amount of space from said viewing area and in optical alignment with said viewing area for directly, continually monitoring said free falling particulate matter and providing signals representative thereof;
means for encasing said preselected space from said viewing area to said monitoring means, said encasing means having reflecting means therein for providing a top view of said particulate matter as said particulate matter passes through said viewing area thereby permitting said monitoring means to indirectly, continually monitor the top view of said particulate matter; and
means operably connected to said monitoring means for receiving said signals therefrom and providing pictorial information sufficient to clearly view said particulate matter at different magnifications as well as enable said fall velocity of said particulate matter to be determined.

2. A fall velocity indicator/viewer as defined in claim 1 further comprising means removably insertable within said port for providing grid lines in said viewing area adjacent said free falling particulate matter in order to aid in said fall velocity determination.

3. A fall velocity indicator/viewer as defined in claim 1 further comprising means adjacent said port for substantially preventing external wind conditions from affecting said free falling particulate matter as it enters said port of said sampling compartment.

4. A fall velocity indicator/viewer as defined in claim 1 further comprising means surrounding said port for limiting said free falling particulate matter entering said port to having trajectories of less than 45° from the vertical.

5. A fall velocity indicator/viewer as defined in claim 4 further comprising means adjacent said port for substantially preventing external wind conditions from affecting said free falling particulate matter as it enters said port of said sampling compartment.

6. A fall velocity indicator/viewer as defined in claim 5 further comprising means removably insertable within said port for providing grid lines in said viewing area adjacent said free falling particulate matter in order to aid in said fall velocity determination.

7. A fall velocity indicator/viewer as defined in claim 6 further comprising means for encasing said monitoring means, said encasing means for said monitoring means having means therein for controlling the temperature therein.

8. A fall velocity indicator/viewer as defined in claim 1 wherein said sampling compartment comprises an outer housing and an inner housing, said inner housing forming a sampling chamber having said viewing area therein, said light providing means being positioned in said outer housing and said inner housing having transparent walls to permit said light to pass therethrough.

9. A fall velocity indicator/viewer as defined in claim 8 wherein said light reflecting means comprises a pair of mirrors situated at preselected angles adjacent the top of said inner housing.

10. A fall velocity indicator/viewer as defined in claim 9 wherein said inner housing contains means for marking the lower boundary of said viewing area.

11. A fall velocity indicator/viewer as defined in claim 10 further comprising means removably insertable within said port for providing grid lines in said viewing area adjacent said free falling particulate matter in order to aid in said fall velocity determination.

12. A fall velocity indicator/viewer as defined in claim 11 further comprising means adjacent said port for substantially preventing external wind conditions from affecting said free falling particulate matter as it enters said port of said sampling compartment.

13. A fall velocity indicator/viewer as defined in claim 12 further comprising means surrounding said port for limiting said free falling particulate matter entering said port to having trajectories of less than 45° from the vertical.

14. A fall velocity indicator/viewer as defined in claim 13 wherein said particulate matter is in the form of snowflakes.

15. A fall velocity indicator/viewer as defined in claim 14 wherein said monitoring means comprises a video camera.

16. A fall velocity indicator/viewer as defined in claim 15 wherein said means for providing said pictorial information is in the form of a television.

17. A fall velocity indicator/viewer as defined in claim 16 further comprising means connected to said television to record the information presented thereon.

* * * * *